United States Patent [19]
Markert et al.

[11] Patent Number: 5,932,771
[45] Date of Patent: Aug. 3, 1999

[54] CARBONYL COMPOUNDS

[75] Inventors: Thomas Markert, Monheim; Ulf-Armin Schaper, Krefeld; Volker Porrmann, Hilden; Werner Faber, Willich, all of Germany; Theo ten Pierik, Le Venlo, Netherlands

[73] Assignee: SmithKline Beecham Corporation, Philadelphia, Pa.

[21] Appl. No.: 09/068,426

[22] PCT Filed: Nov. 4, 1996

[86] PCT No.: PCT/EP96/04797

§ 371 Date: May 8, 1998

§ 102(e) Date: May 8, 1998

[87] PCT Pub. No.: WO97/17314

PCT Pub. Date: May 15, 1997

[30] Foreign Application Priority Data

Nov. 10, 1995 [DE] Germany ............ 195 41 963

[51] Int. Cl.⁶ .......................... C07C 331/00; C07C 45/00
[52] U.S. Cl. .................... 568/300; 568/338; 568/376
[58] Field of Search ................... 568/300, 338, 568/376

[56] References Cited

U.S. PATENT DOCUMENTS 3,993,604  11/1976  Thomas et al. .................... 426/538

FOREIGN PATENT DOCUMENTS 16 43 176  6/1971  Germany .
572 742    2/1976  Switzerland .

*Primary Examiner*—James O. Wilson
*Attorney, Agent, or Firm*—Linda E. Hall; Stephen A. Venetianer; Charles M. Kinzig

[57] ABSTRACT

Carbonyl compounds corresponding to formulae (1a) and (1b)

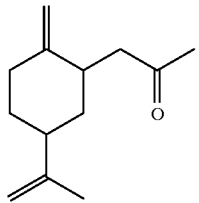

(1a)

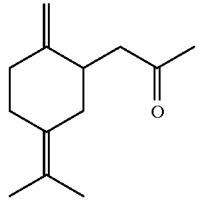

(1b)

16 Claims, No Drawings

CARBONYL COMPOUNDS

BACKGROUND OF THE INVENTION

This invention relates to special carbonyl compounds with the structure shown below and to their use as perfumes.

DISCUSSION OF RELATED ART

Judging by demand, many natural perfumes are available in totally inadequate quantities. For example, 5,000 kg of rose blossoms are required to produce 1 kg of rose oil. The consequences are a seriously limited annual world production and a high price. Accordingly, it is clear that the perfume industry has a constant need for new perfumes with interesting notes in order to add to the range of naturally available perfumes, to make the necessary adaptations to changing fashion trends and to be able to cover the constantly increasing demand for improvements in the odor of products of everyday use, such as cosmetics and cleaners.

Accordingly, it is clear that the perfume industry has a constant need for new perfumes with interesting notes in order to add to the range of naturally available perfumes and to make the necessary adaptations to changing fashion trends and to be able to meet the steadily growing demand for odour enhancers for products of everyday use, such as cosmetics and cleaners.

In addition, there is generally a constant demand for synthetic perfumes which can be favorably produced in a consistent quality and which have desirable olfactory properties, i.e. pleasant, close-to-nature and—qualitatively—novel odor profiles of sufficient intensity, and which are capable of favorably influencing the smell of cosmetic products and consumer goods. In other words, there is a constant need for compounds which have characteristic new odor profiles and, at the same time, high staying power, intensity of odor and emanative power.

DESCRIPTION OF THE INVENTION

It has been found that compounds corresponding to general formula (1a) and/or (1b) meet the requirements stated above in every respect and may advantageously be used as perfumes with differently nuanced odor notes characterized by high staying power:

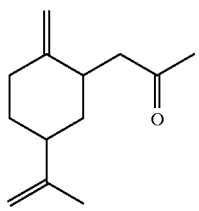

(Ia)

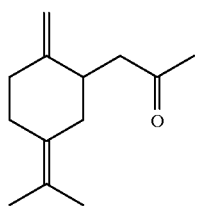

(Ib)

Accordingly, the present invention relates to carbonyl compounds corresponding to formula (1a) and/or (1b).

The present invention also relates to the use of the carbonyl compounds (1a) and/or (1b) as perfumes.

The carbonyl compounds according to the invention are distinguished by an odor characteristic dominated by fruity, green notes reminiscent of ionone. They show excellent stability in formulations used for cosmetics and inexpensive perfumes.

The compounds (I) are produced by known synthesis methods of organic chemistry. The compounds (I) are preferably produced from the corresponding allyl alcohols by the socalled Carroll reaction. These alcohols are perilla alcohol and/or isoperilla alcohol

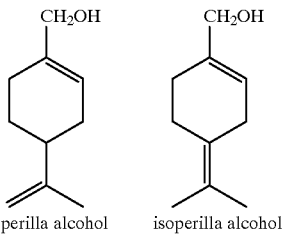

perilla alcohol    isoperilla alcohol

In the context of the present invention, the Carroll reaction is understood to be the conversion of allyl alcohols into ω,δ-unsaturated ketones. In a first variant of the reaction, the allyl alcohol is converted by reaction with acetoacetic ester into the corresponding acetoacetic acid allyl ester, from which α-allyl acetoacetic acid is formed by [3,3]-sigmatropic rearrangement (Claisen rearrangement) and, after thermal decarboxylation, gives the required ω,δ-unsaturated ketone (I). The acetoacetic acid allyl ester may be used as such or may be formed in situ.

In a second variant of the Carroll reaction which is discussed, for example, in a synoptic article by G. B. Bennet (see Synthesis 1977, pages 589–606), the allyl alcohol is reacted with a vinyl ether or an alkoxyalkene. Where vinyl ethers are used, aldehydes are formed; where alkoxyalkenes are used, aldehydes or ketones are formed according to the nature of the alkoxyalkene used. For example, the reaction of cinnamic alcohol with 1-methoxypropene gives an aldehyde while the reaction of cinnamic alcohol with 2-methoxypropene gives a ketone. Acetals or allyl vinyl ether may be assumed to be formed as intermediate compounds in these reactions.

In one preferred embodiment of the invention, perilla and/or isoperilla alcohol is reacted with 2-methoxypropene in the Carroll reaction. The intermediate allyl vinyl ether may be isolated or directly subjected in situ to the subsequent [3,3]-sigmatropic rearrangement to the corresponding ketone (I).

In reaction scheme 1 below, the Carroll reaction is illustrated by way of example for the reaction of perilla alcohol with 2-methoxypropene (for the experimental reaction procedure, see Example 2 below).

Scheme 1

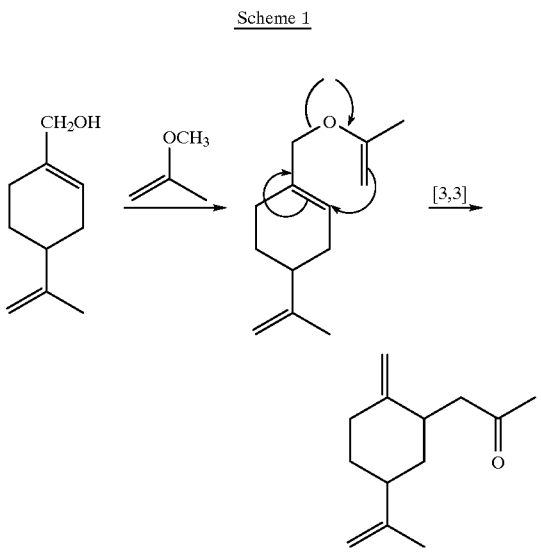

Accordingly, the present invention also relates to a process for the production of the carbonyl compounds (I) by Carroll reaction from perilla and/or isoperilla alcohol. The variant in which the [3,3]-sigmatropic rearrangement proceeds via the allyl vinyl ether during the Carroll reaction and in which the alcohol used at the beginning of the synthesis is reacted with a 2-methoxypropene is preferred because this method of production guarantees particularly high product purity and, hence, the required high olfactory quality of the compounds (I).

The compounds (I) are distinguished a fruity green odor which increases in intensity through aspects of ionone.

In perfume compositions, the compounds (I) strengthen harmony, emanation and naturalness and also staying power, the quantities used being adapted to the particular perfume note required taking the other ingredients of the composition into account.

The fact that the carbonyl compounds (I) have fruity green notes was not foreseeable and, hence, is further confirmation of the general experience that the olfactory properties of known perfumes do not allow any definitive conclusions to be drawn as to the properties of structurally related compounds because neither the mechanism of odor perception nor the influence of chemical structure on odor perception has been sufficiently researched, so that it is not normally possible to predict whether modifications to the structure of known perfumes will in fact lead to changes in their olfactory properties or whether these changes will be positive or negative.

By virtue of their odour profile, the compounds corresponding to formula (I) are also particularly suitable for modifying and enhancing known compositions. Particular emphasis is placed on their extreme intensity of odour which contributes quite generally towards refining the composition.

The compounds corresponding to formula (I) may be combined with many known fragrance ingredients, for example other fragrances of natural, synthetic or partly synthetic origin, essential oils and plant extracts. The range of natural fragrances can thus include both high-volatility and also medium-volatility and low-volatility components while the range of synthetic fragrances may include representatives of virtually every class of compounds. Examples are:

(a) natural products, such as tree moss absolue, basil oil, citrus oils, such as bergamot oil, mandarin oil, etc., mastix absolue, myrtle oil, palmarosa oil, patchouli oil, petitgrain oil, wormwood oil, myrrh oil, olibanum oil (b) alcohols, such as farnesol, geraniol, linalool, nerol, phenylethyl alcohol, rhodinol, cinnamic alcohol, sandalore [3-methyl-5(2,2,3-trimethylcyclopent3-en-1-yl)-pentan-2-ol], sandela [3-isocamphyl-(5)-cyclohexanol]

(c) aldehydes, such as citral, Helional®, α-hexyl cinnamaldehyde, hydroxycitronellal, Lilial® [p-tert.butyl-α-methyldihydrocinnamalde-hyde], methylnonyl acetaldehyde (d) ketones, such as allylionone, α-ionone, β-ionone, isoraldein, methyl ionone (e) esters, such as allylphenoxyacetate, benzyl salicylate, cinnamyl propionate, citronellyl acetate, citronellyl ethoxylate, decyl acetate, dimethylbenzyl carbinyl acetate, ethyl acetoacetate, hexenyl isobutyrate, linalyl acetate, methyl dihydrojasmonate, vetiveryl acetate, cyclohexyl salicylate (f) lactones, such as gamma-undecalactone, 1-oxaspiro[4.4]-nonan-2-one and various other components often used in perfumery, such as ketone musk, indole, p-methan-8-thiol-3-one, methyl eugenol, Ambroxan.

It is also remarkable how the compounds corresponding to formula (I) round off and harmonize the odour notes of a broad range of known compositions without unpleasantly dominating them in any way. 4-Phenyl-hexan-2-one is particularly effective in this regard.

The compounds (I) according to the invention contain chirality centres so that they may exist in various spatial forms. The compounds according to the invention accumulate as mixtures of the corresponding isomers in the course of typical syntheses and are used in this form as perfumes/fragrances.

The compounds according to the invention or mixtures thereof may be used in fragrance compositions in quantities of 1 to 70% by weight, based on the mixture as a whole. Mixtures of compounds (I) according to the invention and compositions of this type may be used both for perfuming cosmetic preparations, such as lotions, creams, shampoos, soaps, salves, powders, aerosols, toothpastes, mouthwashes, deodorants, and also in alcohol-based perfumery (for example colognes, toilet waters, extracts). The compounds according to the invention or mixtures thereof may also be used for perfuming commercial products, such as detergents, fabric softeners and textile treatment preparations. For perfuming the various products, the compositions are added in an olfactorily effective quantity, more particularly in a concentration of 0.05 to 2% by weight, based on the product as a whole. However, these values are not intended to represent limits because the experienced perfumer can also obtain effects with even lower concentrations or can build up new complexes with even higher doses.

The following Examples are intended to illustrate the invention without limiting it in any way.

EXAMPLES

Nomenclature

Perilla alcohol=(4-isopropenylcyclohex-1-en-1-yl)-methane

Isoperilla alcohol=(4-isopropylidenecyclohex-1-enyl)-methanol

Example 1

Reaction of β-pinene oxide to form a mixture of perilla alcohol and isoperilla alcohol Materials:

1) 102 g β-pinene oxide (0.67 mole), technical quality (92%; Acros)

2) 500 ml demineralized water
3) 200 ml dry ice

Method: 102 g of -pinene oxide were emulsified in 500 ml of water in a 2 liter glass beaker and dry ice was introduced in portions into the resulting emulsion. The exothermic reaction was continued for 6 hours until monitoring of the reaction by GLC indicated no further reaction. The reaction product was then extracted from the aqueous phase with ether, the combined organic phases were washed with water, dried over magnesium sulfate and freed from solvent in a rotary evaporator. After addition of 0.45 g of p-pyridinium tosylate, 90.4 g of crude product were transferred to a bulb-tube distillation apparatus and slowly distilled over in a high vacuum at furnace temperatures of 140 to 175° C.

65.1 g of crude product were obtained and were further purified by fractional distillation in a spinning-band column. Separation into perilla alcohol and isoperilla alcohol was also carried out in the spinning-band column. The NMR and IR spectra corresponded to literature data.

Example 2

Reaction of a mixture of isoperilla alcohol and perilla alcohol to form 1-(5-isopropylidene-2-methylenecyclohexyl)-2-propanone and 1-(5-(2'-prop-2'-enyl)-2-methylenecyclohexyl)-2-propanone Materials:
4) 75 g (0.49 mole) perillalisoperilla alcohol mixture from Example 1
5) 42 g (0.57 mole) isopropenyl methyl ether (92%, Acros)
6) 150 g cyclohexane (99%)

Method: Components 4) to 6) were introduced into a 500 ml steel autoclave insert and rendered inert at room temperature under an excess nitrogen pressure of 10 bar. After a reaction time of 7 hours at 190° C./30 bar, no more educt could be detected by gas chromatography so that the reaction was terminated. The reaction mixture was freed from solvent in a rotary evaporator. 95.6 g of crude product were prepurified by bulb-tube distillation and fractionated in a spinning-band column. The main fraction of 51.8 g contained a mixture of the required isomers in a purity of 95%. Boiling point of the mixture: 57–58° C./0.03 mbar.

Odor description: fruity, green, ionone

Composition Example: DPG=dipropylene glycol

| Parts by weight | | |
|---|---|---|
| 1 | Ambroxan | (Henkel) |
| 3 | Oxyphenylone | |
| 5 | Allylamyl glycolate | |
| 5 | Eugenol, 10% in DPG | |
| 5 | Damascenone, 10% in DPG | (Firmenich) |
| 7 | Damascone Beta, 10% in DPG | (Firmenich) |
| 9 | Aldehyde C14 sog. | |
| 15 | Vanillin | |
| 20 | Bergamot oil berg.-free | |
| 20 | Floramat | (Henkel) |
| 25 | Heliotropin | |
| 25 | Dimethylbenzyl carbinyl acetate | |
| 40 | Cyclohexyl salicylate | (Henkel) |
| 45 | Troenan | (Henkel) |
| 50 | Sandelice | (Henkel) |
| 70 | Hedione | (Firmenich) |
| 140 | Iso E Super | (IFF) |
| 190 | Isoraldein 70 | (Givaudan-Roure) |
| 275 | Galaxolide 50 DEP | (IFF) |
| 50 | Dipropylene glycol | |
| 1000 | | |

The raspberry note of the basic composition was supported, rounded off and clearly enhanced by replacing the 50 parts by weight of dipropylene glycol with the substance of Example 2.

What is claimed is:

1. A carbonyl compound corresponding to formula (1 a)

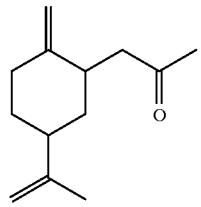

(1a)

2. A carbonyl compound corresponding to formula (1 b)

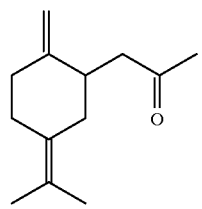

(1b)

3. A mixture of carbonyl compounds corresponding to formulae (1a) and (1b)

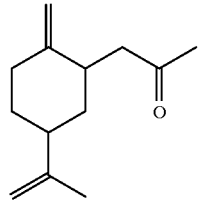

(1a)

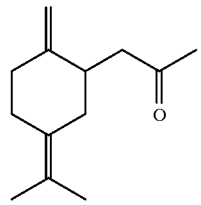

(1b)

4. A perfume composition containing a carbonyl compound corresponding to formula (1a)

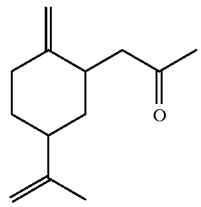

(1a)

5. A perfume composition containing a carbonyl compound corresponding to formula (1b)

(1b)
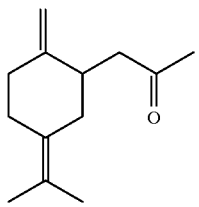

(1b)
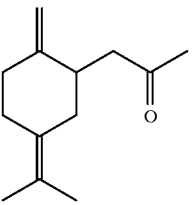

6. A perfume composition containing a mixture of carbonyl compounds corresponding to formulae (1a) and (1b)

(1a)
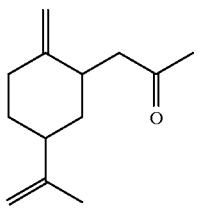

(1b)
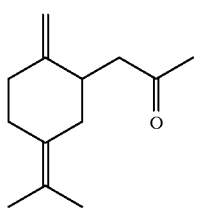

7. A perfume composition as in claim 4 wherein said carbonyl compound is present in an amount of from 1 % to 70% by weight, based on the weight of said composition.

8. A perfume composition as in claim 7 wherein said carbonyl compound is present in an amount of from 1 % to 70% by weight, based on the weight of said composition.

9. A perfume composition as in claim 6 wherein said mixture of carbonyl compounds is present in an amount of from 1 % to 70% by weight, based on the weight of said composition.

10. A process for producing carbonyl compounds corresponding to formulae (1 a) and (1b)

(1a)
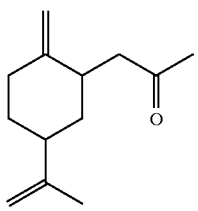

by reacting an allyl alcohol selected from the group consisting of perilla alcohol, isoperilla alcohol, and mixtures thereof with a vinyl ether or an alkoxyalkene per the Carroll reaction.

11. A process as in claim 10 wherein said Carroll reaction comprises the conversion of said allyl alcohol into ω,δ-unsaturated ketones.

12. A process as in claim 11 wherein said allyl alcohol is converted by reaction with acetoacetic ester into the corresponding acetoacetic acid allyl ester, forming α-allyl acetoacetic acid by [3,3]-sigmatropic rearrangement from said allyl ester and, exposing said acetoacetic acid to thermal decarboxylation to obtain said ω,δ-unsaturated ketones.

13. A process as in claim 11 wherein said allyl alcohol is converted by reaction with 2-methoxypropene.

14. A process as in claim 10 wherein said allyl alcohol is reacted with a vinyl ether and converted into an aldehyde.

15. A process as in claim 10 wherein said allyl alcohol is reacted with an alkoxyalkene and converted into an aldehyde or ketone.

16. A cosmetic composition containing from 0.05% to 2% by weight of a carbonyl compound selected from the group consisting of a carbonyl compound corresponding to formula (1a), formula (1b), and mixtures thereof (1a)
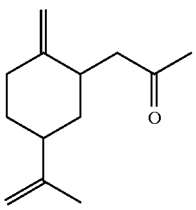

(1b)
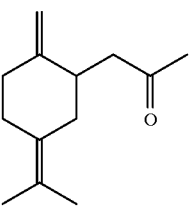

based on the weight of said cosmetic composition.

* * * * *